United States Patent [19]

Kovács et al.

[11] Patent Number: 4,591,379
[45] Date of Patent: May 27, 1986

[54] PLANT GROWTH REGULATORS

[75] Inventors: Antal Kovács; János Erdei; Károly Kováts; László Pólya; Károly Pásztor; János Nagy; Pál Pepó; Péter Pepó, all of Debrecen; György Kiss; István Kajati, both of Budapest, all of Hungary

[73] Assignee: Biogal Gyogyszergyar, Debrecen, Hungary

[21] Appl. No.: 593,040

[22] Filed: Mar. 23, 1984

[30] Foreign Application Priority Data

Mar. 23, 1983 [HU] Hungary ................ 962/83

[51] Int. Cl.$^4$ ............................ A01D 43/42
[52] U.S. Cl. .............................. 71/94; 71/76; 71/77; 71/DIG. 1
[58] Field of Search ................ 71/94, 77, 76

[56] References Cited

U.S. PATENT DOCUMENTS 4,462,993  7/1984  Kovacs et al. .............. 404/180

FOREIGN PATENT DOCUMENTS 3207021  9/1982  Fed. Rep. of Germany.

Primary Examiner—Catherine L. Mills
Attorney, Agent, or Firm—Karl F. Ross; Herbert Dubno

[57] ABSTRACT

The invention relates to plant growth regulators, that is, to compositions influencing the growth of plants. The compositions of the invention contain as active agent a 3,6-diamino-acridine N-glycoside of the formula (I)

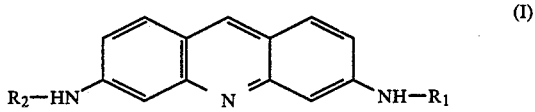

and/or its acid addition salt of the formula (II)

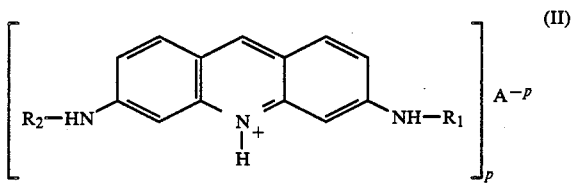

in which formulae
at least one of $R_1$ and $R_2$ stands for an α- and/or β-(D)- and/or α- and/or β-(L)-glucosyl, -galactosyl, -mannosyl, -xylosyl, -arabinosyl, -ribosyl, -6-desoxyglucosyl, -6-desoxygalactosyl, -ramnosyl, -maltosyl, -2-acetamido-2-desoxyglucosyl, -lactosyl, -cellobiosyl, -genciobiosyl or -laminaribiosyl group and the other one represents either a hydrogen atom or one of the enumerated sugar groups;
A is a residue of an acid; and
p stands for 1, 2 or 3.

4 Claims, No Drawings

PLANT GROWTH REGULATORS

The invention relates to plant growth regulators, that is, compositions influencing the growth and development of plants. The compositions of the invention include as active agents a 3,6-diaminoacridine N-glycoside of the formula (I)

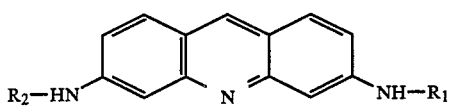

and/or its acid addition salt of the formula (II)

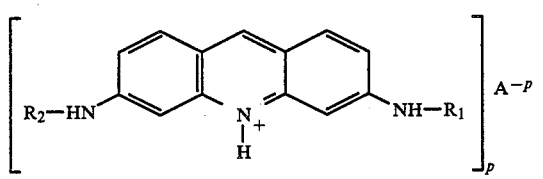

in which formulae
at least one of $R_1$ and $R_2$ stands for an $\alpha$- and/or $\beta$-(D)- and/or $\alpha$- and/or $\beta$-(L)-glucosyl, -galactosyl, -mannosyl, -xylosyl, -arabinosyl, -ribosyl, -6-desoxyglucosyl, -6-desoxygalactosyl, -ramnosyl, -maltosyl, -2-acetamido-2-desoxyglucosyl, -lactosyl, -cellobiosyl, -genciobiosyl or laminaribiosyl group and the other one represents either a hydrogen atom or one of the enumerated sugar groups;
A is a residue of an acid; and
p is equal to 1, 2 or 3.

The compounds of the formula (I) and their acid addition salts of the formula (II) are known from the published German patent application No. 32 07 021, their effect on the growth of plants is not known up to date.

Different processes like the selection of improved varieties, complex plant protection, improving of the soil, fertilizing and watering are widely used in agriculture for improving the yield and the quality of crops in general. A new possibility for increasing the yield of crops was discovered by the use of plant hormones and, respectively, growth regulators (Turner (1972), Outlook Agr. 7,14).

The mechanism of the action of natural plant hormones was studied, and hormone-like acting substances were prepared on an industrial scale. These substances, e.g. auxins, gibberellins, cytokinins, substances deliberating ethylene, inhibitors etc. intervene in the life mechanisms of the plant and thus promote or delay the germination, growth, blooming and fructification of the plant, increase the resistance against frost and dryness, inhibit the lodging of corn, increase the protein content and the content of essential amino acids and so on (T. Dease (1978) World Farm 20, 8–9, 1415; Farm Chemicals (1978) 141, 3, 42; Hungarian patent specification No. 175,568).

The use of growth regulators does not only increase the yield of crops but influences their quality, too, or possesses other agrotechnical advantages (Nickell, L. G. (1982) Plant Growth Regulators, Edn. Springer Verlag Berlin-Heidelberg-New York; U.S. Pat. No. 4,116,675; Japanese patent specification No. 44,676).

Despite the very promising possibilities of application is the use of growth regulators in practice the use is much less wide-spread than one would expect in view of the described advantages. About 70% of the market of the plant growth regulators fall to 8 compositions; namely, most of the substances found up to now are growth inhibiting substances (I.I. Batch: Plant Growth Regulators in Crop Management, Symposium on Bioscience, 20th to 21st Apr., 1982, Szeged, Hungary).

When the commercially available compositions are used in practice, the following disadvantages are to be expected:

in the case of the majority of the compositions the optimally usable quantity falls into a very narrow concentration range, that is, they can easily be "overdosed" and then the desired effect is *not* exerted;

the success of the treatment depends on climatic factors, too;

in case of lignifying plants of several years the condition of the plant in the preceding year is of decisive importance;

some of the regulators are efficacious only if the treatment is performed at a determined vegetative stage of the plant; and the various species of plants react in a different manner on the growth regulators.

Finally, it is a fact that actually remarkable results were attained with plant growth regulators in garden and greenhouse cultivations but there is no actually efficacious stimulator for agriculturally important plants cultivated on large areas, e.g. for maize, soya, rice, wheat (T. Dease (1978) World Farm. 20, 8–9, 1415).

The invention is based on the recognition that the 3,6-diaminoacridine N-glycoside derivatives of the formula (I) influence the growth of plants, first of all they exert a stimulating effect. This recognition is surprising because there is no hint in the technical literature regarding the use of acridine derivatives as growth regulators in agriculture. Numerous acridine derivatives raise big hopes in the cancer research and in case of the known compounds of formula (I) only pharmacological activities were observed up to the present.

It was found that seed-corn and, respectively, seed bulbs treated with a compound of the formula (I) or (II) germinate 1 to 5 days earlier than the untreated control. The degree of stimulation depends on the plant species. In most of the cases the treated seed corns germinate not only more rapidly but also significantly better, that is, the percentual germination (number of germs per 100 seeds) is better. What is of particular importance in the case of seed-corn is to minimize the loss of germination power suffered during storing.

Due to the treatment according to the present invention the development of the root is also more intensive, the total mass of the roots and the number of the side roots increase. The seed-leaves (cotyledon) and the following leaves have a more intensive green color and owing to their higher chlorophyll content the photosynthesis takes place probably more intensively.

By the more rapid germination and the stronger root formation the treated plants possess in most of the cases a higher green mass, too, and not only at the beginning but, depending in case of each plant species, over the complete vegetation period. On the basis of these observations field experiments were performed which showed that the compounds according to the invention increase the crop. Positive results were attained first of all in case of maize, rice, soya, sun-flowers, sugar beets, wheat, poppy and paprika.

In addition to these general observations more or less valid for all the examined plant species the following concrete effects can be stated at the individual species.

In the case of legumes not only the root mass increased strongly but the number of the root bulbs, i.e. rhysobiums, too. In case of poppies the height of the plant was more regular and at the side sprouts there were flowers and, respectively, poppy-heads, too, so that the yield of heads and poppy was increased. Since the alkaloids content was higher, too, significantly more alkaloids could be recovered. In the case of maize the number of the flower branchings increased. In the case of soya the number of the hull storeys was higher. In the case of rice the ears were longer and contained more corns. Sugar beets and wheat showed a significantly higher chlorophyll content. At sun-flowers the stems were longer and thicker, the fruit-plate was bigger, the yield higher.

The complexity of the effect of the active agents according to the invention is surprising. The known growth regulators well-distinguishably exert an action either on the root growth or on the sprout formation or on the development of the generative organs. The acridine derivatives of the formula (I) and their acid addition salts of the formula (II) exert a complex stimulating effect on the whole plant. If e.g. rice is treated by spraying before flowering, not only a more rapid ripening is attained but the crop becomes bigger, too. Numerous growth regulators (e.g. those described in the Hungarian patent specification No. 176,514) exert a yield increasing effect only by inhibiting the vegetative growth and thus enabling a bigger plant density. The active agents according to the invention inhibit in some cases the vegetative growth, too, (poppy, sun-flower), but at the same time they increase the number of the fruit bodies (head, fruit plate) and the concentration of such substances as e.g. the alkaloids.

Finally, a harmony between the genetically depending efficiency of the crop and the environment conditions can be created by using the compounds of the formula (I) and, respectively, their acid addition salts of the formula (II). The available possibilities in this respect are particularly obvious if one thinks of the big difference between the efficiency of a plant in a phytotron and under field conditions.

The compounds of the formula (I) are prepared according to the published German patent application No. 32 07 021. The preparation of the acid addition salts, e.g. the hydrochlorides, hydrobromides, sulfates, phosphates, etc., of the formula (II) is partly described there or they can be prepared according to well-known methods. For influencing the plant growth mixtures of the compounds of the formula (I) and/or their acid addition salts of the formula (II) can also be used.

The plant growth regulators according to the invention include 0.01 to 95 percent by weight of one or more active agent(s) and in addition the usual carriers, auxiliary agents, fillers, extenders, etc. The active agents are converted to preparations, e.g. solutions, dusts, emulsions, suspensions, pastes, granules, etc. in a known manner. These preparations are generally prepared by admixing the active agent(s) with the carriers and/or auxiliary agents and optionally adding surface-active substances, stabilizers and other additives.

As carriers e.g. water; dimethyl sulfoxide; dimethyl formamide; propyl alcohols; ethylene glycol; propylene glycol; hydrocarbons; chlorinated hydrocarbons; ketones like acetone or cyclohexanone; mineral oil fractions as well as mixtures of these solvents can be used. As solid carrier first of all minerals, rock meals, clays, kaolin, talc, diatomaceous earth or organic substances, mainly wastes and by-products of agriculture, e.g. leached beetroot slices, milled maize cob, can be used.

The active agents according to the invention are chemically stable and compatible and therefore they can be used together with other active substances generally used in agriculture, like microelements, insecticides and fungicides.

The compositions of the invention contain, as already mentioned, 0.01 to 95 percent by weight of one ore more active agent(s); a content of 0.01 to 70 percent by weight is preferred. The usual forms ready for use, e.g. spray or pickle, can be prepared by diluting the above-mentioned formulations.

The plant treating is carried out in a known manner e.g. by pickling the seed-corn. The pickling is performed e.g. by submerging the seed-corn into a solution of the active agent; by pickling with a dry or wet powder; by spraying the pickle solution; or by fixing the pickle on the seed-corn with the help of an adhesive agent (e.g. xanthan, see Merck Index IX, compound No. 9719). The active agent enters into the earth together with the seed-corn and, if the seed-corn begins to take up water, into the seed-corn with a very good efficiency. For the pickling preferably 0.5 to 2.5 kg. of active agent are used for one metric ton of the seed-corn.

Since the active agents according to the invention exert a systemic effect, too, they can be applied by pouring onto or spraying the emerged plants. In this way the plants can be treated in a controlled way after the emergence in certain vegetation periods. The optimal time and optimal dose depend on each plant species and can easily be determined by a person skilled in the art by a series of experiments. Owing to the low phytotoxicity of the active agents a possible overdosing is not dangerous. In the case of the application by spraying doses between 0.1 kg. and 3.75 kg. per ha proved to be advantageous. The good solubility of the active agents according to the invention in fat- and wax-like substances makes the penetration into the plant easier. It can still be improved by penetration promoting solvents, e.g. dimethyl sulfoxide.

The activity of the growth regulators of the invention was examined both in laboratory and field tests at numerous plant species. The results described in the following test examples are average values of four replications on small plots in a random arrangement. The identification of the tested compositions (I, II, III, IV and so on) corresponds to the numbering of the formulation examples wherein the preparation of the corresponding compositions is described.

EXAMPLE 1

Seed stimulation of maize (*Zea mays*) in a laboratory test

From formulations containing different active agents pickling liquids of an identical active agent content were prepared by diluting with water. Into 100 ml. each of the treatment liquid 100 seeds each of dry maize seed-corn were merged at a temperature of 25° C. for 16 hours. The dose corresponded to an application rate of 0.5 kg. of active agent per ton of seed-corn.

The examination of the germination was performed according to ISTA (International Rules for Seed Testing; Proc. Int. Seed Test. Ass. 1966, 31, 1–152). Accordingly, the treated seed-corn was stored at a temperature of 25° C. between seed papers wetted with water. The percentual germination was evaluated on the 4th day, the length of the sprout on the 7th day. The control was treated by merging into tap water.

The results are summarized in Table 1. Every result is the average of 3 replications, that is, of 300 seeds.

TABLE 1

| No. of formulation | Active agent | Germination (%) on the 4th day | Length of the sprout (cm.) on the 7th day |
|---|---|---|---|
| I | 3,6-di($\beta$-D-glucopyranosyl-amino)acridine | 100 | 9.8 |
| II | 3-amino-6-($\beta$-D-glucopyranosylamino)acridine hydrochloride | 98 | 7.1 |
| III | 3,6-di($\alpha$-L-ramnopyranosalamino)acridine | 88 | 9.8 |
| IV | 3,6-di($\alpha$-D-ribopyranosyl-amino)acridine | 93 | 9.2 |
| V | 3,6-di($\beta$-lactopyranosyl-amino)acridine | 86 | 9.6 |
| VI | 3-($\beta$-D-glucopyranosylamino)-6-($\alpha$-L-ramnopyranosylamino)-acridine | 100 | 8.7 |
| VII | 3,6-di($\beta$-D-glucopyranosylamino)-acridine and 3-amino-6-($\beta$-D-glucopyranosylamino)-acridine | 100 | 9.8 |
| Control (tap water) | | 85 | 6.4 |

EXAMPLE 2

Seed-corn treatment of rice (field test)

Rice (*Oryza sativa*) to be used for seeding was merged into a solution prepared from compositions VII for 17 hours. The active agent quantity corresponded to an application rate of 2.5 kg./1000 kg. of the seed-corn. The differences observed in the field test in comparison to the control merged into tap water were as follows:
  time of emergence: 5 days earlier
  number of plants per current meter: by 7% higher
  length of the ear: by 10% higher
  corn yield: by 10.8% higher The bigger number of plants on 1 meter points to the fact that the percentual emergence is improved under field conditions, too.

EXAMPLE 3

Seed-corn treatment of sugar beets (field test)

Seed-corns of sugar beet (*Beta vulgaris*) were pickled dry by using composition XI in an application rate of 1.25 kg. active agent for 1 ton of seed-corn. In comparison to the control the following differences were observed regarding the most important parameters:
  time of emergence: 7 days earlier
  number of leaves per plant: by 31% higher
  length of the stem of the developed leaf: by 39% higher
  width of the most developed leaf: by 54.6% broader
  beet weight at the time of the harvest: by 57% higher
  harmful nitrogen content: by 9% less
  yield of pure sugar: by 41.7% higher

EXAMPLE 4

Seed-corn treatment of peas (field test)

Peas (*Pisum sativum*) to be used for seeding were pickled by composition VII, by using 0.5 kg. of active agent were used for 1000 kg. of seed-corn. In comparison to the control the following differences were observed:
  time of emergence: by 6 days earlier
  beginning of flowering: by 4 days earlier
  legume formation: by 1 day earlier
  complete ripening: by 6 days earlier
  period of "tenderness"[(1)]: by 10 days longer
  number of root bulbs (rhysobiums): by 20% higher

[(1)] = The tenderness is a quality parameter during the production of canned legumes. The period of tenderness begins with the pickability and is terminated when the seed begins to become mealy.

EXAMPLE 5

Seed-corn treatment of poppy (field test)

Poppy (*Papaver somniferum*) to be used for seeding was merged into a pickling liquid prepared from composition V for 16 hours. 0.51 kg. of active agent were used for 1000 kg. of seed-corn. In comparison to the control merged into tap water the following differences were observed:
  time of emergence: by 3 days earlier
  growing height of the stalk: by 2 days later
  beginning of flowering: by 2 days earlier
  end of flowering: by 2 days earlier
  weight of the crude leaves: by 32% less
  weight of the crude roots: by 21% less
  height of the plant in flowering state: by 10% less
  number of the sprouts carrying a capsule: by 32.8% higher
  ripening: by 2 days earlier
  yield of capsules: by 32% higher
  yield of poppy seed: by 37% higher
  alkaloid content based on the same quantity of capsules: by 107.1% higher
  morphine content: by 107.1% higher
  codeine content: by 140% higher
  tebaine content: by 52.7% higher
  narcotine content: by 64.7% higher
  narcotaline content: by 84.5% higher

EXAMPLE 6

Post emergence treatment of soya (field test)

Soya plants were treated in a two-leaf state by composition VIII by spraying until running-off. The application rate was 0.1 kg. of active agent/ha. In comparison with the control the following differences were stated:
  height of the plants at the time of the harvest: by 25% higher
  width of the leaves at the time of the harvest: by 32.2% broader
  length of the leaves at the time of the harvest: by 43.2% longer
  distance of the lowest legume from the soil: by 36% higher
  number of the legume levels: nearly double (1.98)
  dry root mass: by 87.36% higher
  yield of green legumes: by 38.7% higher
  number of the leaves at the time of the harvest in % of the maximal number of the leaves: 24.7% more leaves remain on the plant until the harvest

EXAMPLE 7

Seed-corn pickling and ultrasonic treatment (maize; field test)

Maize to be used for seeding was pickled with composition I in an application rate of 0.2 kg. of active agent/1000 kg. of seed-corn and treated with ultrasound for 5 minutes (apparatus of type KLN, vibration head TI, delivered power: 0.7 W./cm$^3$.). In relation to the control only treated with ultrasound but not pickled the following differences were observed:
time of emergence: 2 days earlier
biotic potential of the germ: by 7% higher
height of the plant: by 10% higher
length of the leaf: by 33% higher
width of the leaf: by 28% higher
thickness of the stem: by 8% thicker
number of the maize-ear/parcel: by 8% higher
weight of 1000 corns: by 16% higher
corn/ear: by 25% more In the following some examples for the formulation of the compositions according to the invention are described. By "product form" a commercial formulation is meant which has to be diluted before use. Under "application form" the composition ready for use is understood. The Roman numbers of the compositions correspond to those indicated in the test examples.

PRODUCT FORM I

A composition is prepared from
50 percent by weight of 3,6-di($\beta$-D-glucopyranosylamino)acridine,
40 percent by weight of dimethyl sulfoxide and
10 percent by weight of water.
Before use it is diluted to the desired concentration.

PRODUCT FORM II 5 percent by weight of 3-amino-6-($\beta$-D-glucopyranosylamino)acridine hydrochloride,
1 percent by weight of water and
94 percent by weight of dimethyl sulfoxide
are homogenized. Before use the composition is diluted to the desired concentration.

PRODUCT FORM III 12.5 percent by weight of 3,6-di($\alpha$-L-ramnopyranosylamino)acridine,
65.0 percent by weight of dimethyl sulfoxide and
22.5 percent by weight of water
are homogenized. The composition is diluted by water to the desired concentration before use.

PRODUCT FORM IV 40 percent by weight of 3,6-di($\alpha$-D-ribopyranosylamino)acridine,
50 percent by weight of dimethyl sulfoxide and
10 percent by weight of water
are homogenized. Before use the composition is diluted to the desired concentration.

PRODUCT FORM V 25 percent by weight of 3,6-di($\beta$-lactopyranosylamino)acridine,
65 percent by weight of dimethyl sulfoxide and
10 percent by weight of water
are homogenized. Before use the composition is diluted by water to the desired concentration.

PRODUCT FORM VI 30 percent by weight of 3-($\beta$-D-glucopyranosylamino)-6-($\alpha$-L-ramnopyranosylamino)acridine,
3 percent by weight of propanol and
67 percent by weight of water
are homogenized. Before use the composition is diluted to the desired concentration by water.

PRODUCT FORM VII 15 percent by weight of 3,6-di($\beta$-D-glucopyranosyamino)acridine,
10 percent by weight of 3-amino-6-($\beta$-D-glucopyranosylamino)acridine,
5 percent by weight of ethylene glycol,
2 percent by weight of dimethyl sulfoxide and
68 percent by weight of water
are homogenized. Before use the composition is admixed with a 1 percent by weight solution of the polysaccharide xanthan (or one of the commercially available adhesive agents) in a weight ratio of 1:1 and then diluted with the seed-corn to be treated to the desired concentration (kg. of active agent per ton of seed-corn).

APPLICATION FORM VIII 3,6-di($\beta$-D-glucopyranosylamino)acridine: 0.01 Wt.%
dimethyl sulfoxide: 1.00 Wt.%
water: 98.99 Wt.%
The composition can directly be used for spraying the plants.

PRODUCT AND APPLICATION FORM IX 3,6-di($\beta$-D-glucopyranosylamino)acridine: 95 Wt.%
talc: 5 Wt.%
The composition is diluted at pickling with the seed-corn to be treated to the desired concentration.

PRODUCT FORM X 50 percent by weight of 3,6-di($\beta$-D-glucopyranosylamino)-acridine and
50 percent by weight of kaolin
are homogenized. Before use 2 percent by weight of water are added to the composition and the latter is diluted with the seed-corn to be treated to the desired concentration.

PRODUCT AND APPLICATION FORM XI 3,6-di($\beta$-D-glucopyranosylamino)acridine: 70 Wt.%
talc: 30 Wt.%
Before use the composition is diluted with the seed-corn to be treated to the desired concentration.

What we claim is:

1. A method for regulating the growth of plants which comprises the step of treating the plant or a propagating part thereof with an effective amount of a 3,6-diaminoacridine N-glycoside of the formula (I)

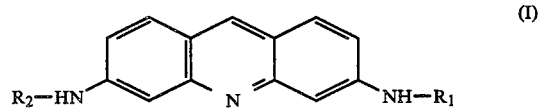

or its agriculturally acceptable acid addition salt of the formula (II)

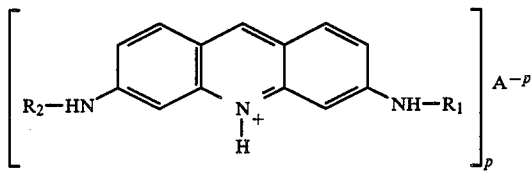

in which formulae at least one of $R_1$ and $R_2$ stands for an α- and/or β-(D)- and/or α- and/or β-(L)-glucosyl, -galactosyl, -mannosyl, -xylosyl, -arabinosyl, -ribosyl, -6-desoxyglucosyl, -6-desoxygalactosyl, -ramnosyl, -maltosyl, -2-acetamido-2-desoxyglucosyl, -lactosyl, -cellobiosyl, -genciobiosyl or -laminaribiosyl group and the other one represents either a hydrogen atom or one of the enumerated sugar groups;

A is a residue of an agriculturally acceptable acid;
p stands for 1, 2 and 3.

2. The method for regulating the growth of plants defined in claim 1 wherein the active ingredient of the Formula (I) or (II) is 3,6-di(β-glucopyranosylamino)acridine, 3-amino-6-(β-D-glucopyranosylamino)acridine hydrochloride, 3,6-di(α-L-ramnopyranosylamino)acridine, 3,6-di(β-lactopyranosylamino)acridine, 3-(β-D-glucopyranosylamino)-6-(α-L-ramnopyranosylamino)acridine, 3-amino-6-(β-D-glucopyranosylamino)acridine or a mixture thereof.

3. The method for regulating the growth of plants defined in claim 1 wherein an agriculturally acceptable aqueous solution of dimethyl sulfoxide is admixed with the active ingredient of the Formula (I) or (II).

4. The method for regulating the growth of plants defined in claim 1 wherein the agriculturally acceptable acid addition salt of the formula (II) is the hydrochloride, hydrobromide, sulfate or phosphate salt.

* * * * *